United States Patent
Highgate et al.

(10) Patent No.: US 7,210,935 B2
(45) Date of Patent: May 1, 2007

(54) EXPANDABLE/CONTRACTABLE COMPOSITION FOR SURGICAL OR DENTAL USE

(75) Inventors: Donald James Highgate, Surrey (GB); Jonathan Anthony Lloyd, Lincs (GB)

(73) Assignee: Dental Root Filling Products Ltd (GB)

( * ) Notice: Subject to any disclaimer, the term of this patent is extended or adjusted under 35 U.S.C. 154(b) by 43 days.

(21) Appl. No.: 10/832,484

(22) Filed: Apr. 26, 2004

(65) Prior Publication Data

US 2004/0234930 A1    Nov. 25, 2004

(30) Foreign Application Priority Data

Apr. 24, 2003   (GB) ................... 0309317.6

(51) Int. Cl.
*A61C 5/02*    (2006.01)

(52) U.S. Cl. .................. 433/224; 433/228.1; 523/116; 523/121

(58) Field of Classification Search ................ 433/224, 433/75, 81, 102, 226, 228.1, 149, 148; 106/35; 520/523, 109, 105, 113–120
See application file for complete search history.

(56) References Cited

U.S. PATENT DOCUMENTS

| | | | | |
|---|---|---|---|---|
| 4,565,722 A | * | 1/1986 | Highgate et al. ......... 428/36.9 |
| 5,171,278 A | * | 12/1992 | Pisharodi ................ 128/898 |
| 5,222,817 A | * | 6/1993 | Glazier .................. 384/559 |
| 5,460,621 A | * | 10/1995 | Gertzman et al. .......... 604/358 |
| 5,527,181 A | * | 6/1996 | Rawls et al. ............. 433/149 |
| 5,573,400 A | * | 11/1996 | Asher .................... 433/136 |
| 5,674,241 A | * | 10/1997 | Bley et al. .............. 623/1.2 |
| 5,700,277 A | * | 12/1997 | Nash et al. .............. 606/213 |
| 5,862,861 A | * | 1/1999 | Kalsi .................... 166/277 |
| 5,964,744 A | * | 10/1999 | Balbierz et al. .......... 604/530 |
| 6,083,259 A | * | 7/2000 | Frantzen ................. 623/1.15 |
| 6,127,597 A | * | 10/2000 | Beyar et al. ............. 606/86 |
| 6,425,898 B1 | * | 7/2002 | Wilson et al. ............ 606/108 |
| 6,450,815 B1 | * | 9/2002 | Weisman ................. 433/220 |
| 6,530,951 B1 | * | 3/2003 | Bates et al. ............. 623/1.45 |
| 6,758,863 B2 | * | 7/2004 | Estes et al. ............. 623/17.16 |
| 2002/0013620 A1 | * | 1/2002 | Kujawski ................. 623/1.16 |
| 2002/0096833 A1 | * | 7/2002 | Czaplicki et al. ......... 277/316 |
| 2003/0139800 A1 | * | 7/2003 | Campbell ................. 623/1.15 |

FOREIGN PATENT DOCUMENTS

| | | | |
|---|---|---|---|
| GB | 1566552 | * | 5/1980 |
| GB | 2 139 898 A | | 11/1984 |
| GB | 2 340 430 A | | 2/2000 |

* cited by examiner

*Primary Examiner*—Cary E. O'Connor
(74) *Attorney, Agent, or Firm*—Saliwanchik, Lloyd & Saliwanchik

(57) ABSTRACT

A composition, suitable for surgical or dental use, which can expand and/or contract in at least one direction without similar expansion or contraction in another direction, comprises an inner and an outer portion, the portions differing in their expansion properties and/or the extent to which they are prestressed.

11 Claims, 5 Drawing Sheets

EXPANDABLE/CONTRACTABLE COMPOSITION FOR SURGICAL OR DENTAL USE

FIELD OF THE INVENTION

This Invention relates to a composition, suitable for surgical or dental use.

BACKGROUND TO THE INVENTION

GB-A-2139898 describes a deformable polymeric composition which can absorb liquid and thereby expand or contract in one direction without similar expansion or contraction in another direction. In particular, GB-A-2139898 describes an insert plug for dental cavities, which can absorb liquid and thereby expand radially without expanding axially. The material is such that it does not expand isotropically or uniformly (as a percentage of its initial dimensions) in every direction but, instead, has different expansion properties in different directions. Since the composition does not expand axially, it does not load the final cosmetic surface applied to the outer surface of the cavity and, since it expands laterally, it is possible to achieve a good fit by selection out of a relatively small number of inserts, relative to traditional rubber inserts. Other compositions described in GB-A-2139898 are surgical inserts, such as breast implants and nerve approximation sheaths.

GB-A-2340430 describes a dental insert plug of a prestressed hydrophilic material, the material prestressed by the application of pressure in the temperature range of 100 to 160° C.

Although insert plugs such as those described above achieve a relatively good fit, gaps may still remain between the walls of the cavity and the insert plug. Consequently, a sealant must be used to seal these gaps. There still remains the need for compositions whose shape change and/or expansion properties can be accurately controlled and predetermined.

SUMMARY OF THE INVENTION

It has been discovered that by using a combination of materials which differ in their expansion properties and/or extent of prestressing, the expansion and shape change properties of a composition can be accurately predetermined and controlled. For example, a dental insert plug of the invention may be such that the use of a separate sealant is no longer necessary.

Accordingly, the invention is a composition, suitable for surgical or dental use, which can expand and/or contract in at least one direction without similar expansion or contraction in another direction, the composition comprising an inner and an outer portion, the portions differing in their expansion properties and/or the extent to which they are prestressed.

A composition may be in the form of an insert plug, suitable for dental use, the plug being able to expand radially substantially without expanding axially. In this case, the plug is preferably tapered. Preferably, at least the outer portion is radio-opaque.

DESCRIPTION OF THE PREFERRED EMBODIMENTS

Figure 1:
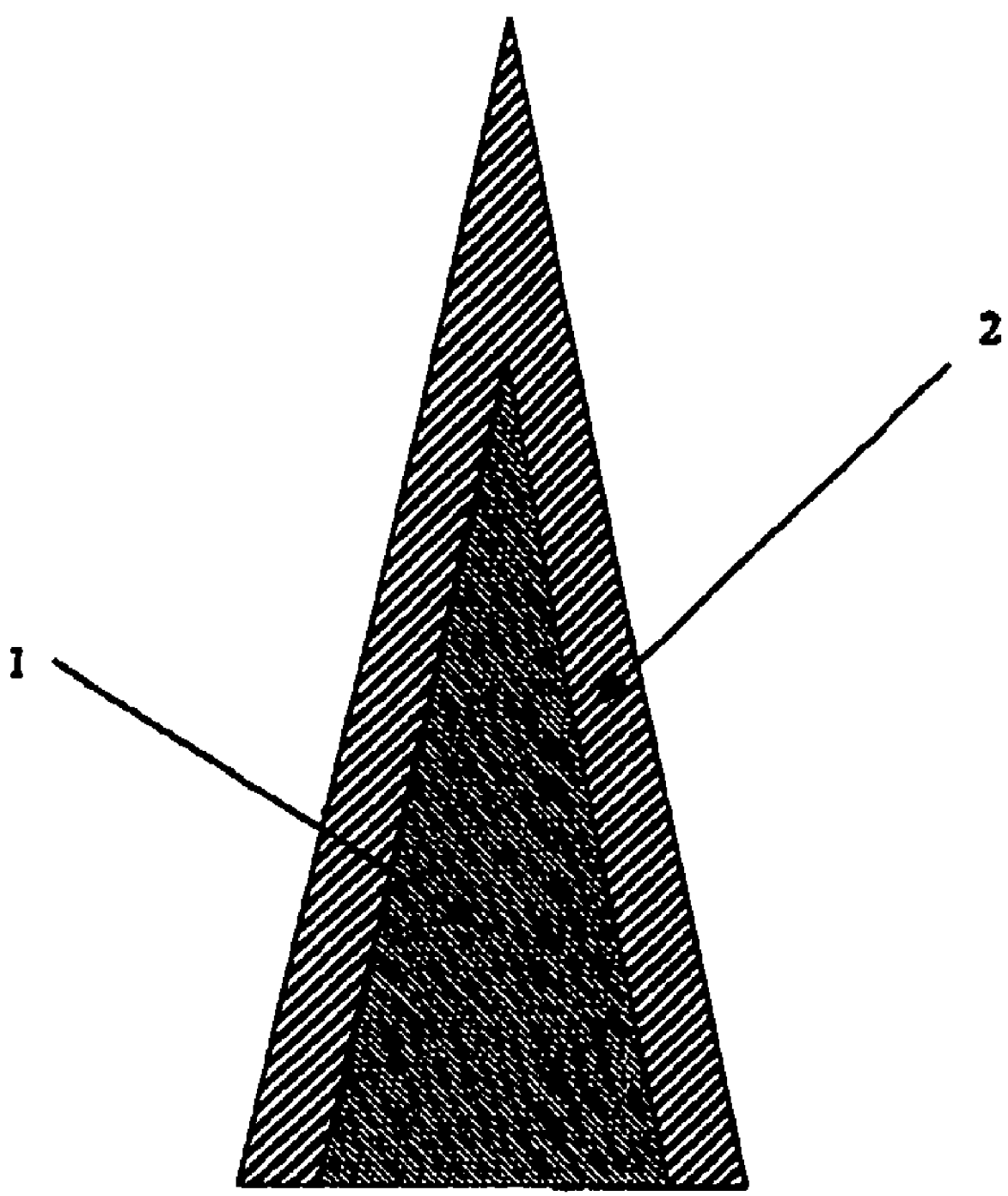
FIG. 1 is a cross-sectional view of a composition of the invention which is in the form of a dental insert plug, the plug comprising an outer portion of uniform thickness.

The present invention is particularly relevant to compositions in the form of dental insert plugs. However, surgical applications, for example breast implants and nerve approximation sheaths, are also envisaged. A composition of the invention for use as a breast implant may be essentially cylindrically shaped, the composition able to expand along its axis without similar radial expansion.

The portions must differ in at least their expendability or extent of prestressing. Thus, one portion may be expandable and the other non-expandable, or they may both be expandable but differ in their rates of expansion. Similarly, one portion may be prestressed and the other non-prestressed, or they may both be prestressed but to different exents. A composition of the invention may be composed of two or more materials differing in their expansion and/or prestressing properties. Thus the inner portion may comprise a plurality of materials which differ in such properties compared with the outer portion and/or with one another.

In a preferred embodiment of the Invention, the inner and outer portions are both expandable. The outer portion may comprise a material having an optimised rate of expansion, allowing it to conform accurately with the complex internal structure of, for example, a root canal. Additionally or alternatively, the outer portion may comprise a material which is more malleable than the inner core, so that an accurate fit can be achieved.

Preferably, the inner and/or outer portion comprises a prestressed hydrophilic material. The material may be relaxed by the action of heat and/or hydration. The purpose of prestressing is to change the initial shape so as to arrive at some other desired shape upon hydration or heating. A prestressed material may or may not also undergo expansion or contraction when hydrated. Upon heating and/or hydration, the material becomes less rigid and the shape imposed by prestressing relaxes. Where heat is used, the material preferably relaxes at a temperature of between 30 to 100° C., preferably 40 to 50° C. The inner portion is preferably a copolymer obtainable by the polymerisation of acrylonitrile (AN) and N-vinyl-2-pyrrolidone (VP). The outer portion is preferably a hydrophilic polymer obtainable by the polymerisation of methyl methacrylate (MMA), hydroxyethyl methacrylate (HEMA), N-vinyl pyrrolidone (VP), acrylonitrile (AN) comonomers. Hydrophilic polymers, and their prestressing, are described in, for example, GB-A-2139898.

The outer portion may be unstressed and thus able to expand isotropically upon hydration. Alternatively, the outer portion may be prestressed, either to the same degree as the core or to a different extent, in the latter case, the outer portion may change shape independently of the core.

The outer portion may be formed by any suitable method known in the art, for example by adhesion, co-extrusion, casting or dipping. The outer portion may be formed using a multi-stage process in which a mould is partially filled with the polymerisable components of the outer portion. The components are then polymerised and the remaining space filled with the components of the inner core; these are then polymerised.

A preferred method of manufacture of a composition of the invention comprises the following steps:

(a) cast the core in an mould using an appropriate material (for example 1:1 AN-VP incorporating 10% water), polymerise with 2 mRad of ionising radiation from a Cobalt 60 source optionally in the presence of 0.1–5% of allyl methacrylate as a crosslinking agent and/or 0.1 to 1% of AIBN as an initiator (at this stage, the 'core' may be prestressed to eliminate any tendency to expand axially on hydration);

(b) reassemble the initial cast point in a mould, off-setting the point from the mould by a predetermined amount (typically 1 mm) as set by the use of a shim of suitable thickness, inject the monomers necessary to produce the outer component of the composite point and allow to stand for between 2 to 60 minutes (preferably 5 minutes); and (c) polymerise and cross-link the outer layer of the composite structure, i.e. the additional hydrophilic polymeric material is polymerised in situ.

In step (b), the standing time allows the monomers to diffuse into the existing point material to form an interpenetrated hydrophilic structure, preventing delamination during any subsequent prestressing, or hydration or handling processes.

In step (c), the polymerisation and cross-linking reactions can be achieved either by additional gamma irradiation, by the use of UV radiation in the presence of a suitable UV initiator the mould being UV transparent, or by subjecting the mould to a controlled heating cycle (e.g. in a water bath, in the presence of a suitable thermal initiator (such as AIBN).

The inner and/or outer portion may be fabricated in a material which is not hydrophilic but is capable of being accurately prestressed, the prestressing being relaxed by the action of a suitable control "trigger", e.g. by heating. For example, the insert may comprise a memory metal core coated with a non-prestressed elastomeric outer layer (e.g. polyurethane), the relaxation caused, in this case, by heating.

The composition may be impregnated with an antibiotic and/or an anti-fungal agent to prevent degradation such as that caused by bacteria or fungi present in the root canal.

For reasons of commercial acceptability, a dental insert plug of the invention is preferably in the shape of an industry standard such as a 4% to 6% tapered circular cone. The inner portion can be of a different geometry to the outer, resulting in a coating of varying thickness. For some uses, the outer coating preferably increases in thickness for smaller diameters.

The invention will now be described, by way of example only, with reference to the accompanying drawings.

FIG. 1 depicts an insert plug comprising an inner portion 1 composed of a prestressed hydrophilic material. The outer portion 2 is of uniform thickness and also comprises a separately prestressed hydrophilic material.

Upon hydration, both the inner and outer positions expand. Since the two portions have been prestressed separately, the change of shape experienced by one portion is independent from the other.

Figure 2:
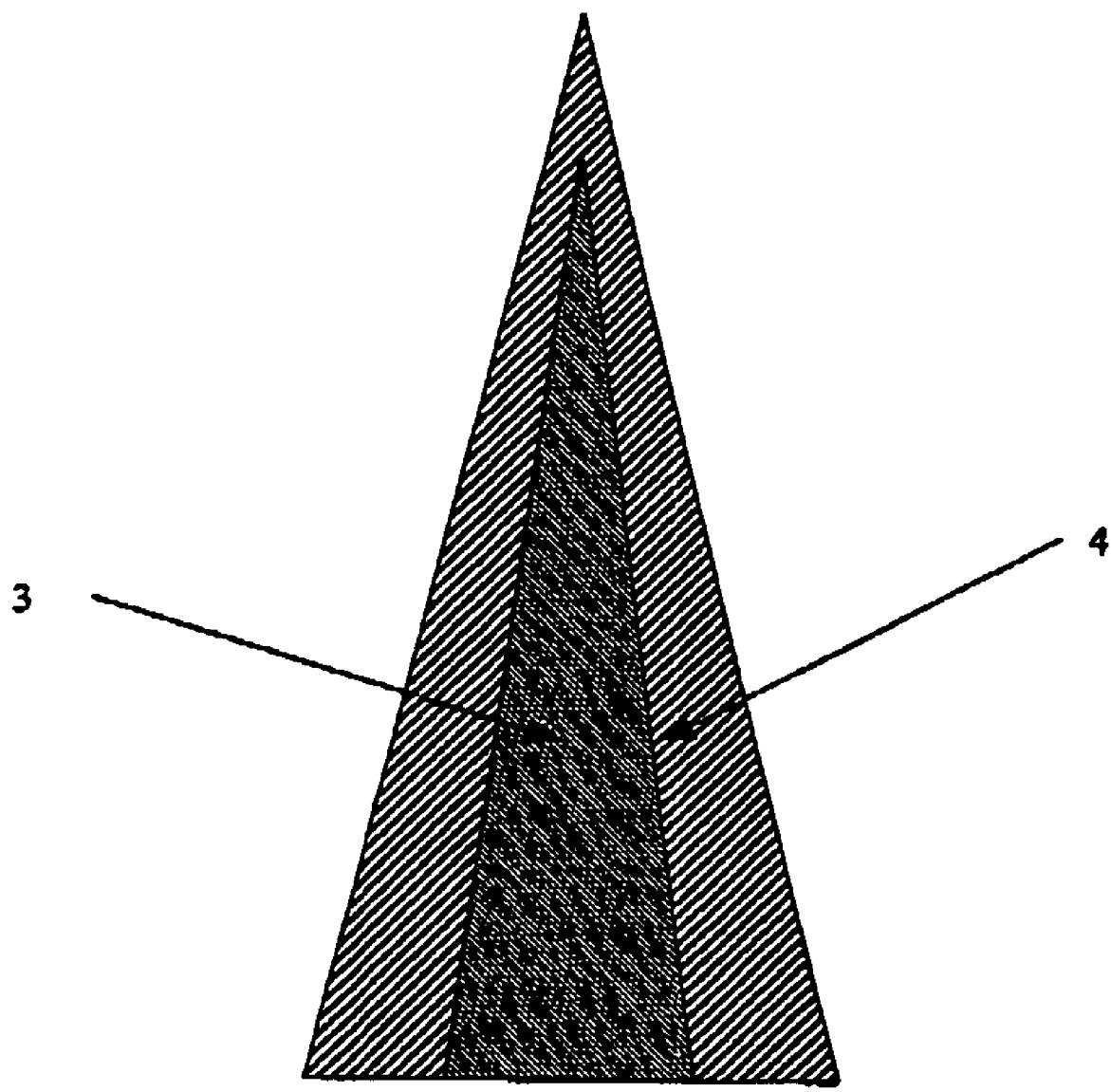
FIG. 2 is a cross-sectional view of a composition of the invention in the form of a dental insert plug, the plug comprising an outer portion which gradually increases in thickness with the diameter of the inner portion.

FIG. 2 shows an insert plug comprising an inner portion 3 which is a hydrophilic material in the form of a 5.75% tapered core. The outer portion 4 also comprises a hydrophilic material, and is in the form of a 6% tapered core. The thickness of the outer portion thus increases with the diameter of the inner portion.

Figure 3:
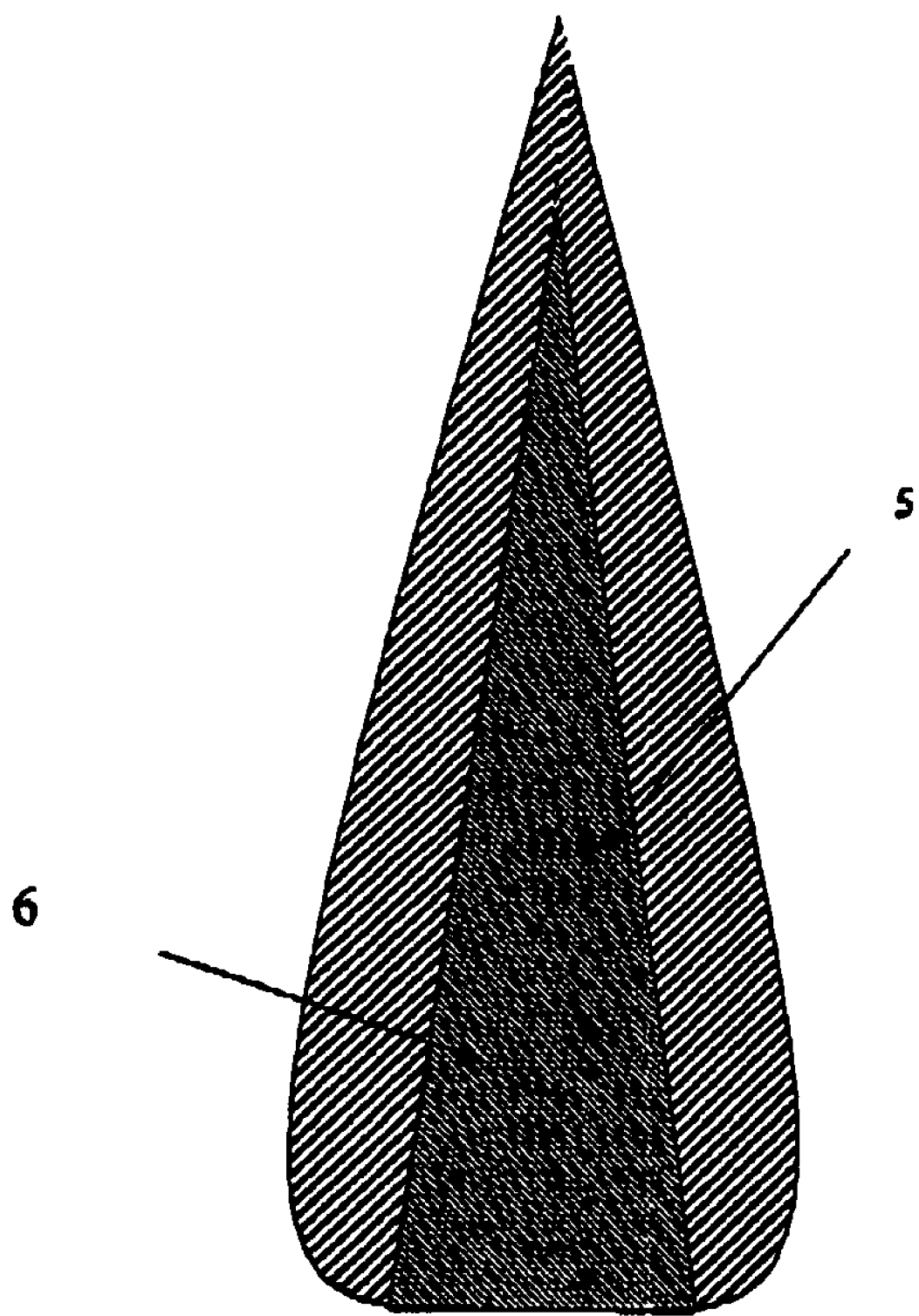
FIG. 3 is a cross-sectional view of a composition of the invention which is in the form of a dental insert plug, the outer portion of which is of irregular thickness.

An insert plug comprising an outer portion 5 of varying thickness is shown in FIG. 3. The composition may be obtained by using a different mould to form the outer portion than that used for forming the core 6.

The geometry of the outer portion is such that greater expansion occurs in particular regions of the plug. This type of insert would be particularly useful for filling cavities in molar teeth since molar teeth have complex root canal shapes and non-uniform cross-sections.

Figure 4:
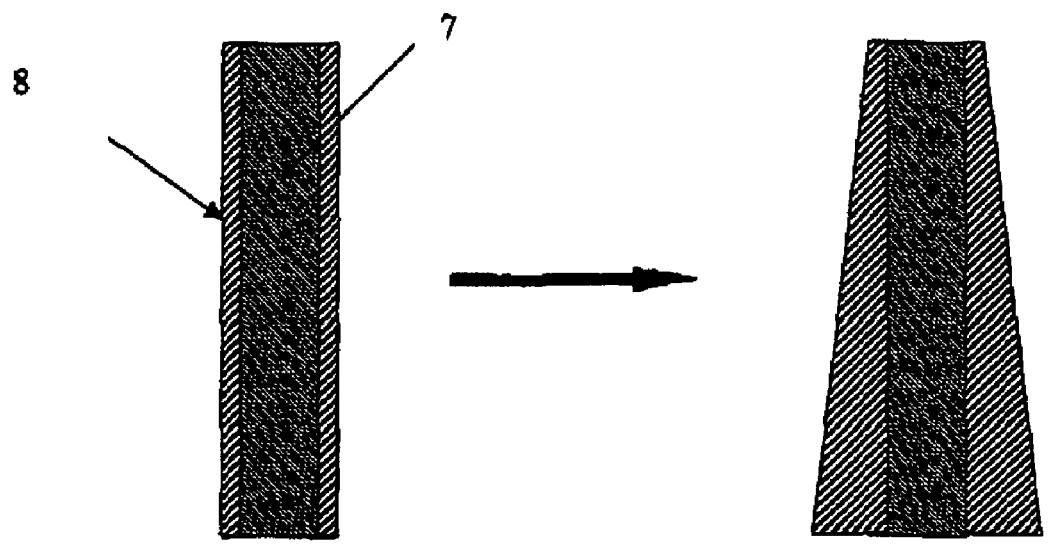
FIG. 4 is a cross-sectional view of a composition of the invention comprising a non-expandable, non-prestressed inner portion.

FIG. 4 shows a composition of the invention, comprising a non-expandable, non-prestressed inner portion 7. Upon hydration of the composition (as represented by the arrow), the outer portion 8 expands anisotropically.

Figure 5:
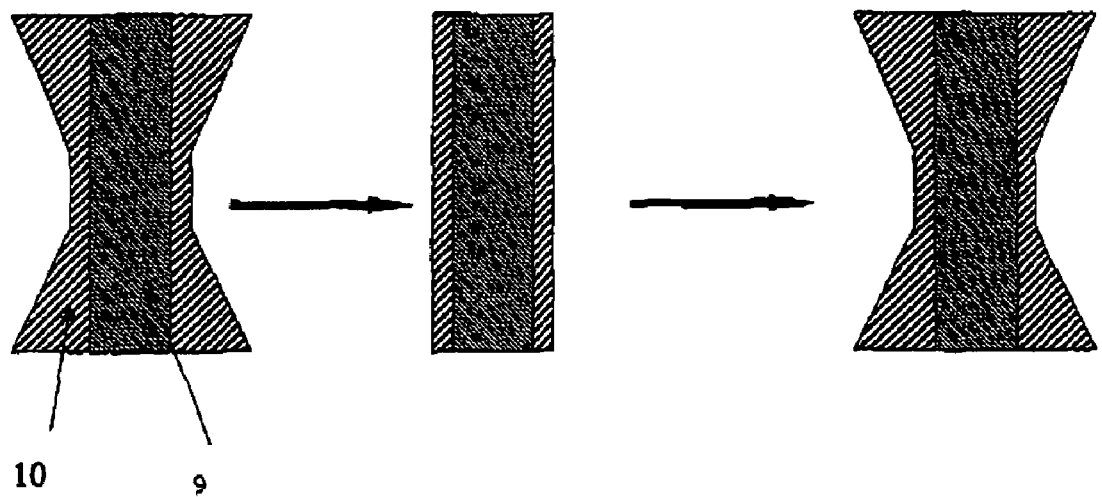
FIG. 5 is a cross-sectional view of a composition of the invention, comprising a non-expandable, non-prestressed inner portion.

FIG. 5 shows a composition similar to that of FIG. 4. The first arrow represents the step of forming the composition by prestressing the outer portion 10, rather than the inner portion 9, of a "dumb bell" shape composition. Shape recovery, as represented by the second arrow, may be achieved by hydration or heating.

Figure 6:
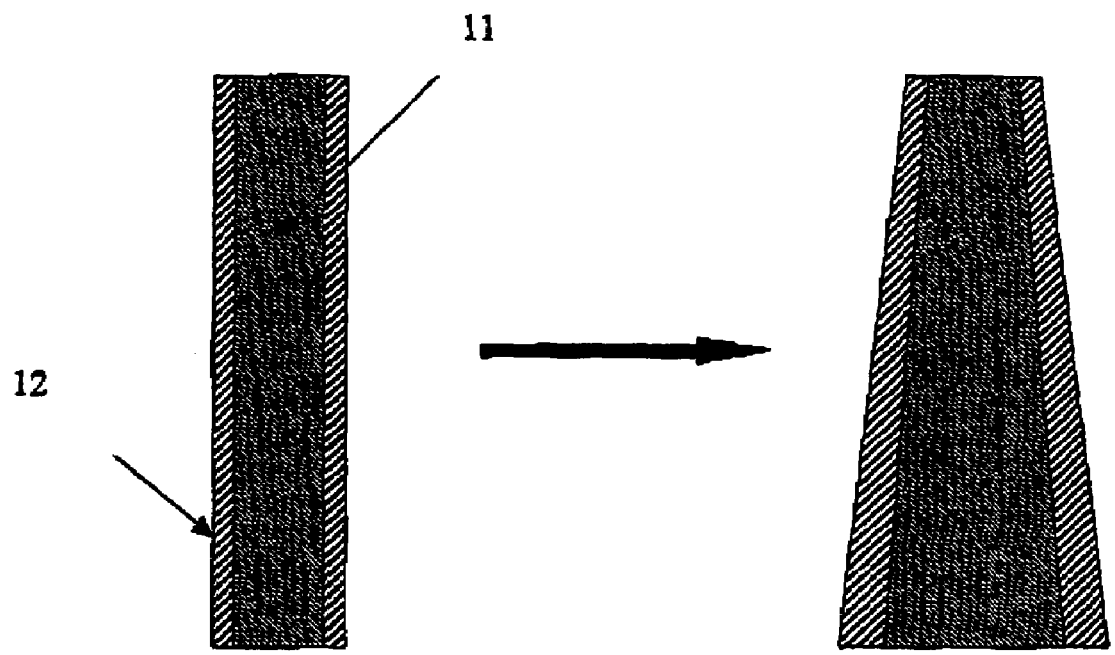
FIG. 6 is a cross-sectional view of a composition of the invention comprising an expandable inner portion.

FIG. 6 shows a composition of the invention comprising an expandable inner portion 11 and an outer portion 12. The inner portion expands anisotropically upon hydration (represented by the arrow).

Figure 7:
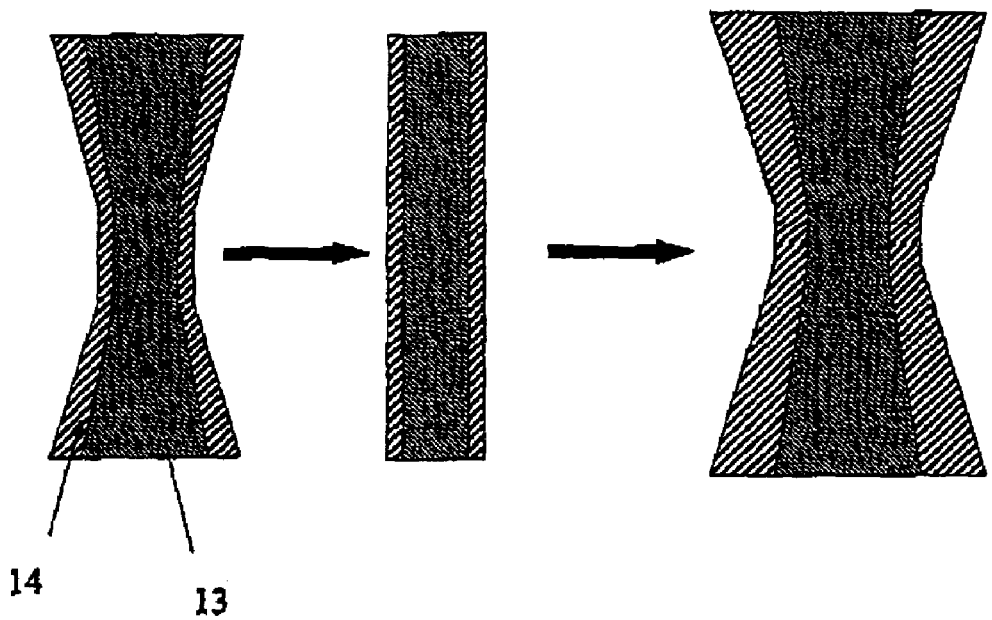
FIG. 7 is a cross-sectional view of a composition of the invention, comprising a prestressed, expandable inner portion.

FIG. 7 shows a composition similar to that of FIG. 6. The composition is formed by prestressing the inner portion 13, rather than the outer portion 14 (as represented by the first arrow) a dumb-bell-shaped composition. Shape recovery may be achieved by hydration or heating. If recovery is achieved by hydration, as represented by the second arrow, then the composition also undergoes expansion.

The invention claimed is:

1. A composition, suitable for surgical or dental use, which can expand and/or contract in at least one direction without expansion or contraction in another direction, the composition comprising an inner and an outer portion, the portions differing in their expansion properties and/or the extent to which they are prestressed, wherein the inner portion is in contact with the outer portion at an interface comprising an interpenetrating hydrophilic structure, wherein said composition is solid.

2. The composition, according to claim 1, wherein one of the inner and outer portions is expandable, and the other is not.

3. The composition, according to claim 1, wherein one of the inner and outer portions is prestressed, and the other is not.

4. The composition, according to claim 1, wherein the inner portion is prestressed, and wherein the outer portion is not prestressed.

5. The composition, according to claim 1, wherein the inner portion comprises a hydrophilic material that expands upon hydration.

6. The composition, according to any of claim 1, wherein the inner portion comprises a memory metal.

7. The composition, according to claim 1, wherein the outer portion comprises a hydrophilic material that expands upon hydration.

8. The composition, according to claim 1, wherein the outer portion is more malleable than the inner portion.

9. A composition, which can expand and/or contract in at least one direction without expansion or contraction in another direction, the composition comprising an inner and an outer portion, the portions differing in their expansion properties and/or the extent to which they are prestressed, wherein the inner portion is in contact with the outer portion at an interface comprising an interpenetrating hydrophilic structure, which is in the form of an insert plug, suitable for dental use, and which can expand radially substantially without expanding axially, wherein said composition is solid.

10. The composition, according to claim 9, wherein the plug is tapered.

11. The composition, according to claim 9, wherein at least the outer portion is radio-opaque.

* * * * *